Figure 1A:
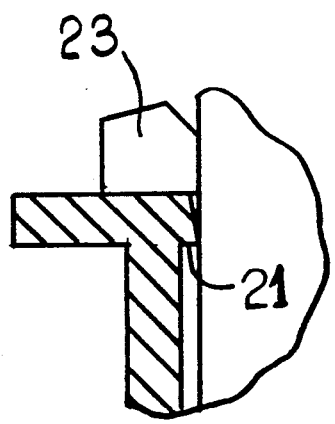
Figure 1B:
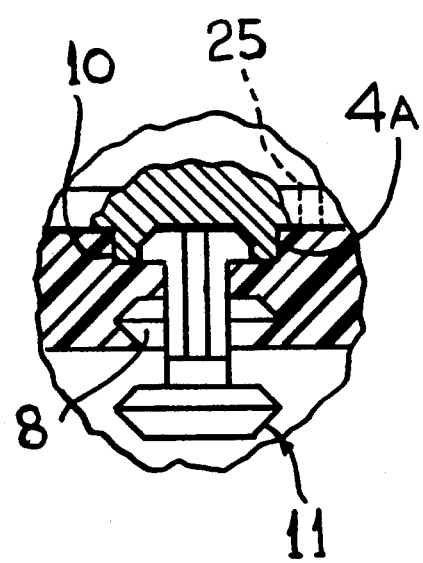

United States Patent [19]

Spanner et al.

[11] Patent Number: 5,026,346
[45] Date of Patent: Jun. 25, 1991

[54] NON-REUSABLE SYRINGE

[75] Inventors: John R. Spanner, Cheltenham; Nonton Hill-Male, Winchcombe; Harinder S. Soomal, Bexley, all of England

[73] Assignee: Dowty Seals Limited, Tewkesbury, England

[21] Appl. No.: 220,465

[22] Filed: Jul. 18, 1988

[30] Foreign Application Priority Data

Jul. 21, 1987 [GB] United Kingdom ............. 8717170
Jan. 21, 1988 [GB] United Kingdom ............. 8801358
Mar. 19, 1988 [GB] United Kingdom ............. 8806595

[51] Int. Cl.$^5$ ............................................. A61M 5/00
[52] U.S. Cl. .................................. 604/110; 604/218; 604/236
[58] Field of Search ............... 604/110, 218, 238, 228, 604/187, 247, 237, 236

[56] References Cited

U.S. PATENT DOCUMENTS 3,986,645 10/1976 Baldwin et al. ............. 604/238 X
3,998,224 12/1976 Chiquiar-Arias .
4,391,273 7/1983 Chiquiar-Arias .
4,687,467 8/1987 Cygielski ..................... 604/110
4,863,427 9/1989 Cocchi ......................... 604/110

FOREIGN PATENT DOCUMENTS 210386 6/1984 Fed. Rep. of Germany ...... 604/110
2298340 8/1976 France .
2571261 4/1986 France .
1454540 11/1976 United Kingdom .
2015883 9/1979 United Kingdom .
2117249 10/1983 United Kingdom .
2187961 9/1987 United Kingdom .
2191405 12/1987 United Kingdom .
WO83/00438 2/1983 World Int. Prop. O. .

Primary Examiner—John D. Yasko
Attorney, Agent, or Firm—Young & Thompson

[57] ABSTRACT

A syringe comprising a barrel with means for positioning a needle at a forward end thereof, a plunger displaceable within the barrel, sealing means to maintain the integrity of a dispensing chamber forwardly of the barrel, wherein the plunger has associated disabling means to render the sealing means ineffective after a first use of the syringe.

10 Claims, 6 Drawing Sheets

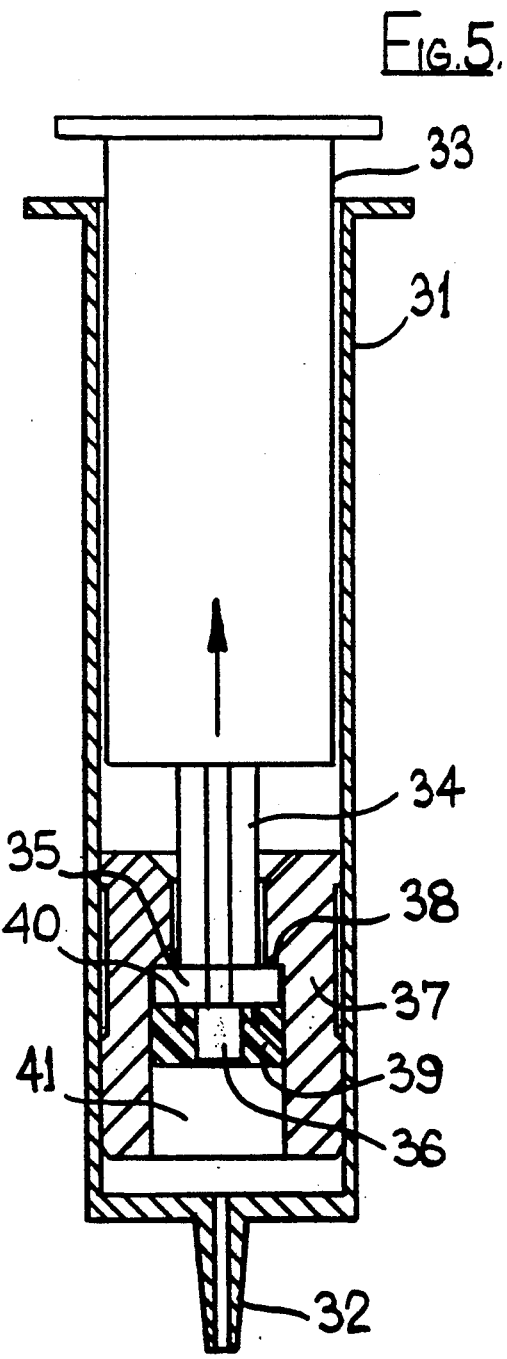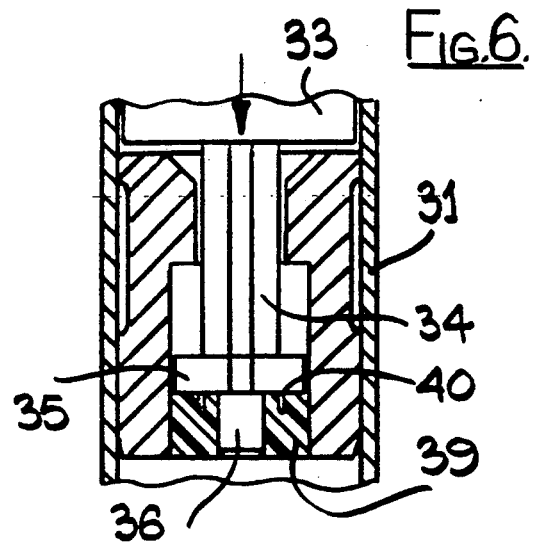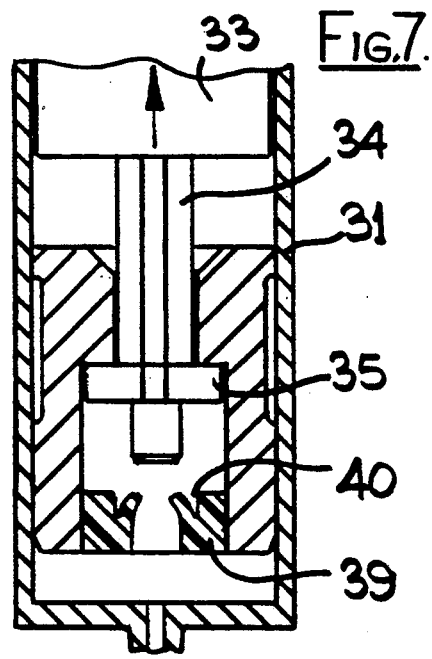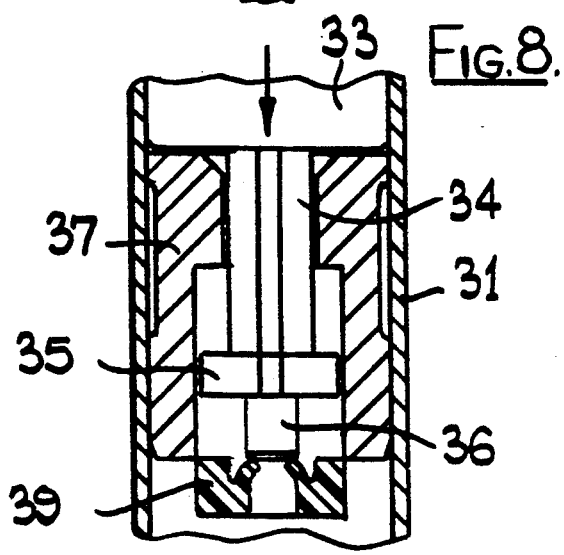

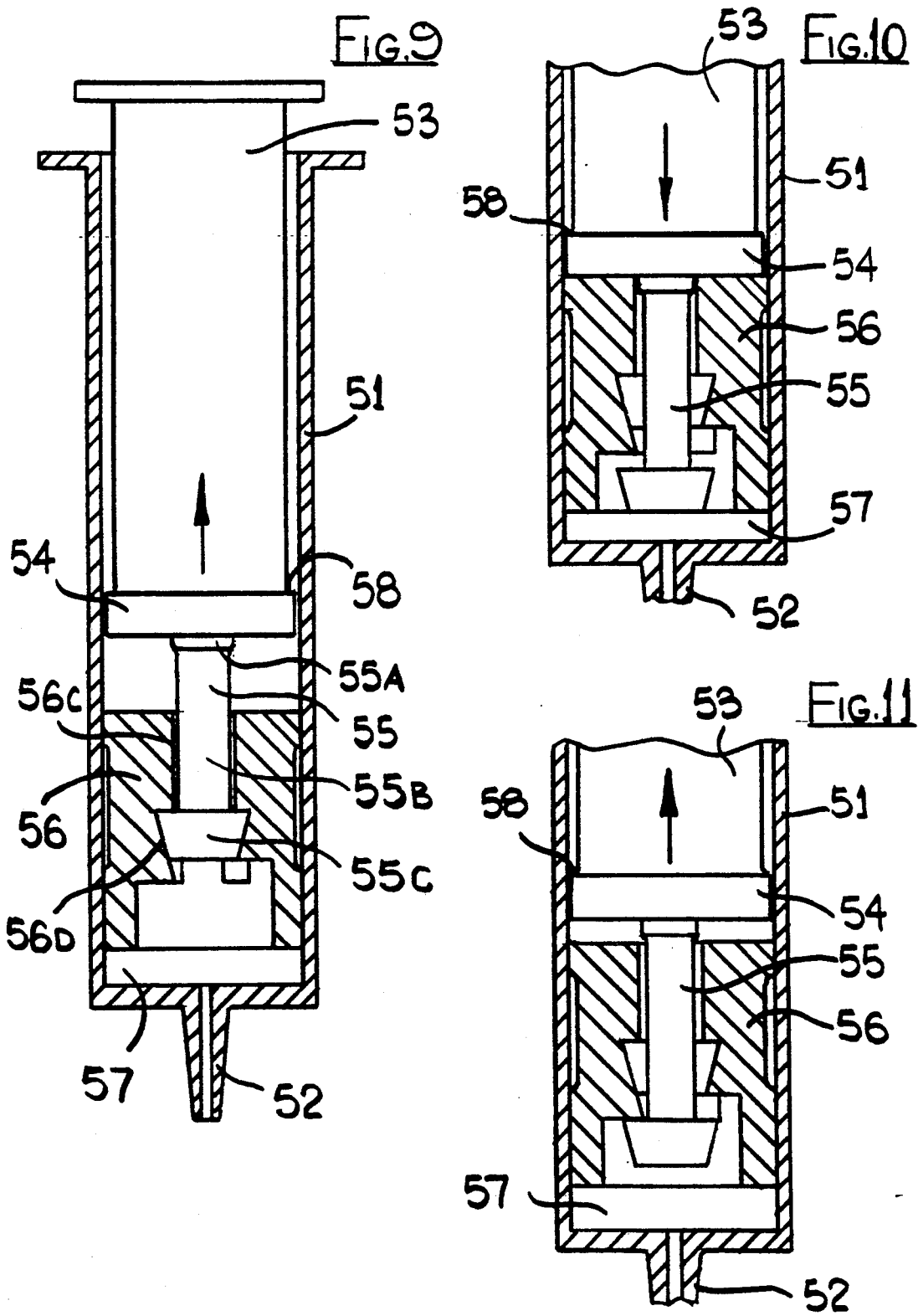

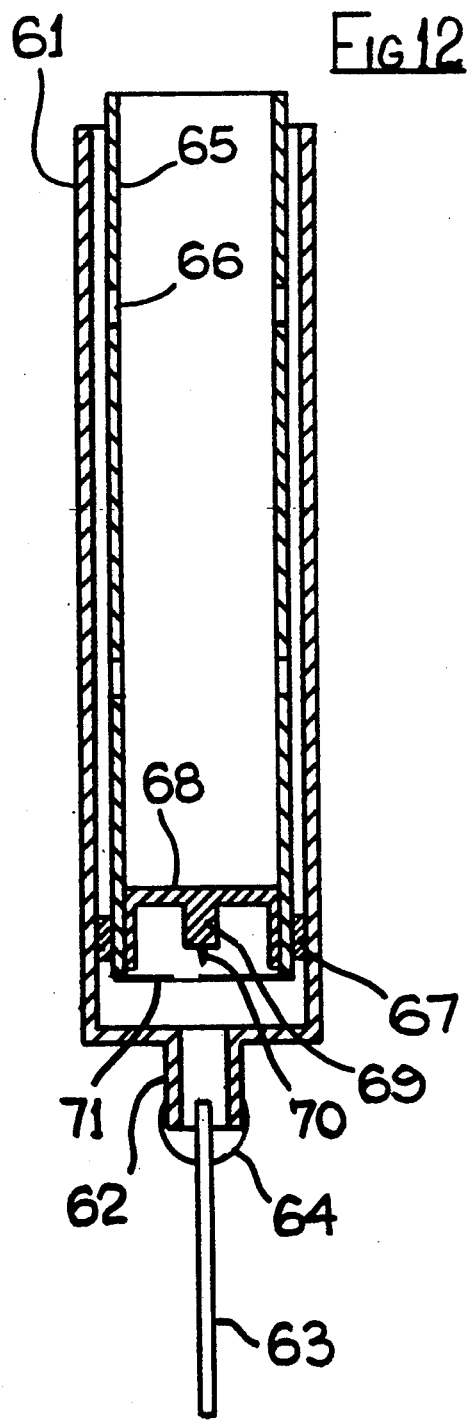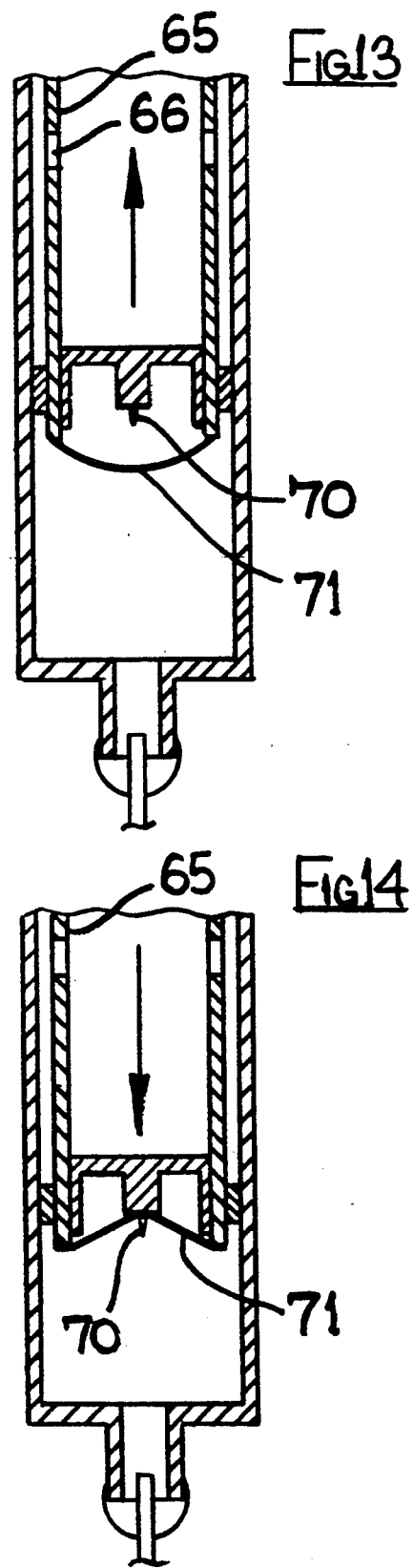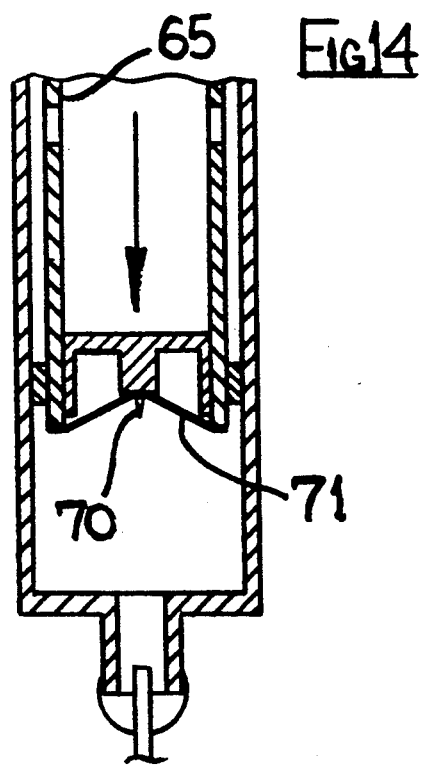

NON-REUSABLE SYRINGE

This invention relates to medical syringes and more particularly to syringes whose operation is prevented after a first use.

Normal types of syringe employ a cylindrical barrel with a hollow needle at an otherwise closed end thereof and a plunger slidable within the barrel in sealing engagement with the internal wall of the barrel so as to form a dispensing chamber between the plunger and the end of the barrel carrying the needle. The sealing engagement between the plunger and the barrel is usually effected by a simple rubber seal held on the end of the plunger adjacent the dispensing chamber.

There are obvious health hazards associated with multiple use of a single syringe by different persons; in particular, such use can readily cause the spread of viruses from one person to another. Various attempts have therefore been made to render a syringe inoperable after a first use.

Some of these attempts have centered on destroying the integrity of the dispensing chamber during a first use, for example by puncturing the wall of the barrel by a prong attached to the plunger. Others have centered on physically trapping the plunger in the barrel by mechanical stops employing cam surfaces or similar devices and preventing its withdrawal.

However, such attempts have generally not proved successful and determined potential reusers of the currently available syringes can often be successful. Commonly, for example, the syringes are only disabled if and when the plunger is fully inserted into the barrel.

The present invention is concerned with a syringe in which the integrity of the dispensing chamber is destroyed to render the syringe inoperative after a first use.

In accordance with the invention, there is provided a syringe comprising a barrel with means for positioning a needle at a forward end thereof, a plunger displaceable within the barrel, sealing means to maintain the integrity of a dispensing chamber forwardly of the barrel, wherein the plunger has associated disabling means to render the sealing means ineffective after a first use of the syringe.

It is important for the disabling means to be associated with the plunger so that the non-effectiveness of the sealing means can generally be achieved through a relatively small displacement of the plunger and is not dependent on a complete insertion of the plunger into the barrel.

Preferably the sealing means, in addition to the disabling means, is associated with the plunger so that relative movement between the plunger and the barrel causes interaction between the plunger, the sealing means and the disabling means and results in the sealing means being ineffective after a first use of the syringe.

In a first embodiment of the invention, the sealing means incorporates an insert as disabling means which is adapted for displacement within or from the sealing means during a first use of the syringe and thereby subsequently render the sealing means inoperative in any attempted re-use of the syringe.

Preferably the sealing means comprises a disc of elastomeric material, normally rubber, attached to the forward end of the plunger, i.e. that end closest to the needle. Attachment to the plunger can be achieved in any convenient way such as a stretch fit over a forwardly extending flange of the plunger. Preferably, however, the attachment allows for a small relative movement between the sealing means and the plunger along the axis of the barrel.

In addition, the arrangement of plunger/barrel should preferably be such that, in use, there are air passageways to allow access of atmospheric air to the side of the sealing means remote from the needle.

In a first use of a syringe of this embodiment of the invention, i.e. with the insert in position in the sealing means, liquid is drawn into the dispensing chamber by placing the needle in the liquid and partially withdrawing the plunger from the barrel. When the correct amount has been drawn in, the liquid is injected by returning the plunger into the barrel. Clearly, the nature of the insert should allow it to be retained in place in the sealing means during the plunger withdrawal stage, i.e. against the partial vacuum caused in that stage, but to be displaced within or from the sealing means during the plunger injection stage. Equally, the sealing means should be such that, in the plunger injection stage, the integrity of the sealing means and hence of the dispensing chamber must be retained in order to complete the injection of fluid during the syringe first use but destroyed thereafter.

This is achieved in preferred syringes of the invention by:

i) providing an insert in a surface of the sealing means defining or adjoining the dispensing chamber and causing it to be held therein prior to use of the syringe by retaining means, for example a retaining lip, of a cavity in the sealing means of a size complementary to that of the insert ii) maintaining in the injection stage, a seal between the plunger and the sealing means (and hence maintain the integrity of the dispensing chamber) when the insert has been displaced.

In a preferred aspect of the first embodiment of the invention, the insert is substantially plate or disc-shaped; preferably such an insert is manufactured from a more rigid material, for example metal or plastic, than that of the sealing means itself.

In this aspect, it is particularly preferred that the insert has an extension portion on an end remote from the dispensing chamber so that on displacement of the insert into the dispensing chamber, the extension portion is retained by the sealing means to avoid the insert blocking or otherwise interfering with the syringe mechanism, for example by preventing the plunger completing a full stroke to the base of the barrel. It is essential that the insert does not continue to maintain the integrity of the sealing means following its displacement; the insert is therefore preferably provided with ports or other air passageways to allow communication between the dispensing chamber and the barrel rearwardly of the sealing means and hence with atmosphere.

In a second preferred aspect of the first embodiment of the invention, the sealing means comprises a hollow, preferably cylindrical, seal element mounted about the forward end of the plunger (or about an extension thereof) such that limited relative axial movement is allowed between the plunger and the seal element and wherein disabling means in the form of an insert made from elastomeric material is mounted about a forward end of the plunger or extension thereof) and being in an interference fit with the inside surface of the seal element. Preferably the insert is either of general cylindrical or "O" ring shape.

In such an aspect, it is preferred that the insert is designed to remain in place about the plunger and within the seal element during a first withdrawal of the plunger but to be displaced to the forward end of the seal element during a first injection of the plunger. Means should be provided to prevent re-positioning of the insert about the plunger, and preferably on a second injection also to eject the insert from the inside of the seal element, so that the integrity of the seal is broken.

Preferably the means to prevent repositioning of the insert about the plunger comprises slits to cause splaying of the insert or alternatively protrusions or flanges which physically prevent repositioning once the insert has been displaced. Such protrusions or flanges could usefully be present on a generally "O" ring shaped insert.

In a third preferred aspect of the first embodiment of the invention, the insert is integral with, or fixed to, the plunger rather than being independent of the plunger. In such an aspect, it is preferred that the sealing means is movable relative to the plunger from a first position in which the plunger maintains the integrity of the seal to a second position in which the plunger is displaced relative to the sealing means to render the sealing means inoperative after a first use of the syringe.

Preferably the part of the plunger associated with the sealing means is an extension portion at that end of the plunger closest to the needle. In such a preferred embodiment the sealing means is preferably an elastomeric seal positioned about the plunger extension and slidably movable relative to the plunger extension in the direction of the longitudinal axis of the barrel.

Advantageously, the sealing means possesses a cavity or groove within which a portion of the plunger, or an extension thereof, can in a first position form an effective seal between the plunger and the sealing means. Ideally, this is achieved by having the cavity and the plunger portion of complementary shape and size to ensure a tight fit of the latter in the former.

However the nature of association between the sealing means and the plunger is such that on a first use of the syringe the sealing means can be moved relative to the plunger to a second position in which the seal integrity is lost and cannot be regained on any attempted use of the syringe subsequent to a first use.

In preferred embodiments having complementary plunger portion and sealing means cavity/groove as above, this second position is achieved by causing the plunger portion to be dislodged from the cavity/groove in the sealing means during the plunger injection stage, i.e. when the plunger is being moved further inside the barrel. Preferably, means are provided to ensure that no subsequent sealing occurs between the plunger and the sealing means.

Most preferably, the plunger portion is an extension of a main plunger of standard design and is centrally mounted on the base of the main plunger. The association between the plunger portion and the sealing means can be achieved by mounting the sealing means, for example an elastomeric seal of substantially cylindrical shape around the plunger portion in a manner which allows for relative sliding movement along the longitudinal axis of the seal.

The plunger portion can conveniently possess an enlarged end which in the first position is received in a correspondingly shaped and sized cavity in the sealing means. To assist in retaining the respective components in their first position, this enlarged end and the cavity most preferably possess angled surfaces, for example those provided by respective conical or frusto-conical shapes. However, the size of the angle as well as the properties of the elastomeric sealing means will determine the threshold required to allow the second position to be achieved when needed.

In accordance with a second embodiment of the invention, the sealing means includes a diaphragm which defines part of the contour of the dispensing chamber, and the disabling means comprises puncturing means associated with the sealing means and arranged to impart physical damage to the diaphragm when the plunger is depressed, thereby to destroy its sealing function; preferably the puncturing means comprises a pin or blade.

Conveniently, the puncturing means can comprise at least one pin or blade positioned at the forward end of the plunger, with the diaphragm positioned across the forward end of the plunger ahead of the puncturing means.

In the case of a diaphragm positioned across the forward end of the plunger, the diaphragm is preferably so dimensioned and of such a material that it is capable of displacement from a convex configuration when the plunger is being withdrawn to a concave configuration when the plunger is depressed. This enables the diaphragm to be positioned well away from the disabling means while the plunger is being withdrawn but to be positively brought into physical contact with the disabling means when the plunger is depressed.

With regard to syringes of the invention in general, supplementary means to prevent the plunger being withdrawn completely from the barrel may be employed to ensure non-reuse of the syringe, for example by providing external lugs on the plunger which necessarily engage in use with internal lugs on the barrel.

Syringes are normally supplied with a gap between the sealing means and the base of the barrel. To maintain the integrity of the sealing means of the syringes of the invention against accidental movement of the plunger during storage and/or transport leading to premature displacement of the insert, preferred embodiments possess a device to maintain such a gap, for example by having a lug on the end of the plunger remote from the sealing means and a complementary groove in the end of the barrel remote from the needle so that full insertion of the plunger into the barrel can only be achieved when the lug and groove are aligned in use of the syringe.

Figure 1:
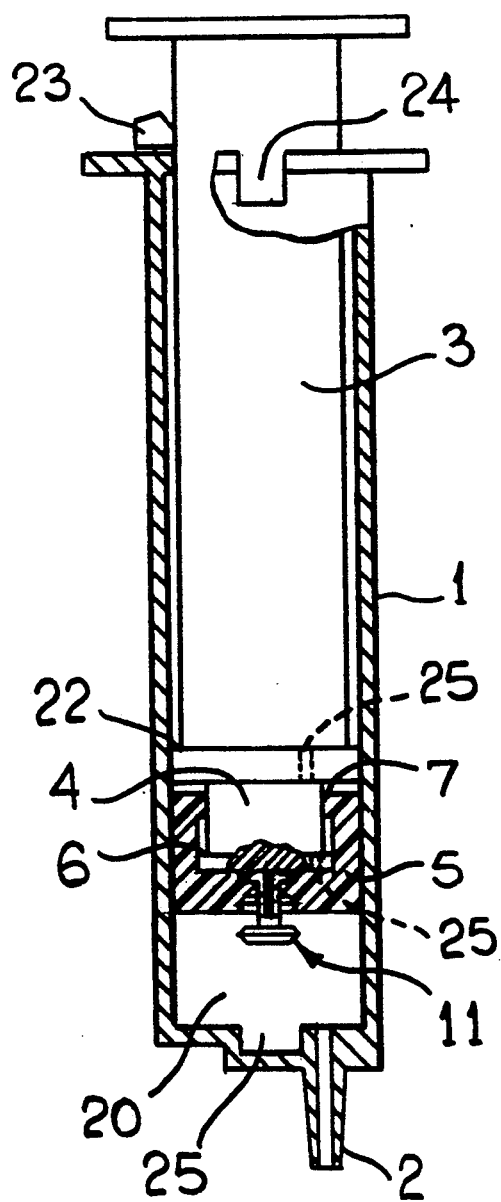
Figure 2:
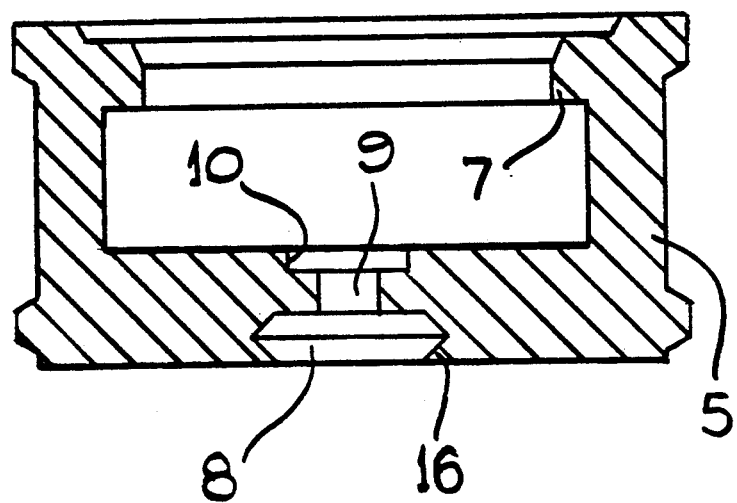
Figure 3:
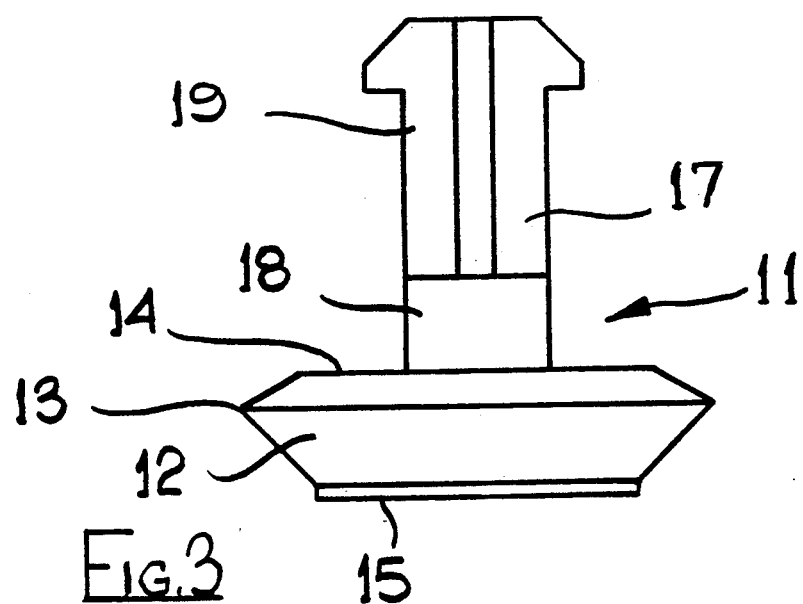
Figure 4:
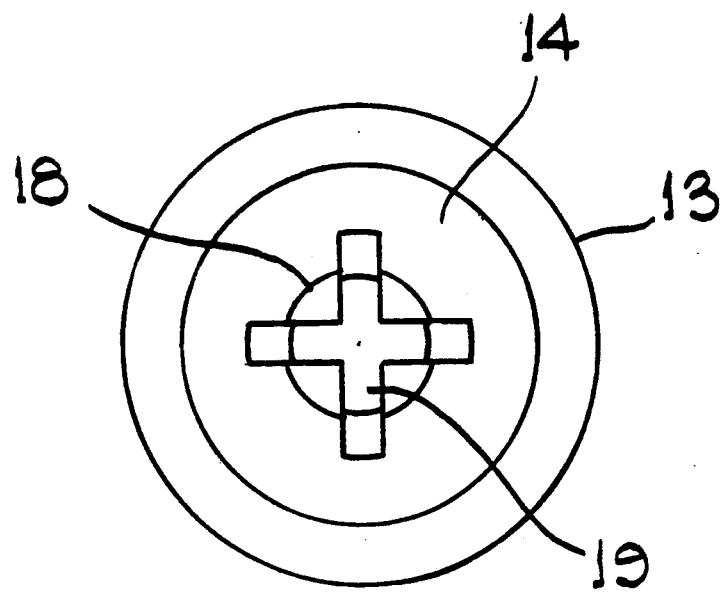

For a better understanding of the invention, reference will now be made, for the purposes of exemplification only, to the accompanying drawings in which:

FIG. 1 shows a sectional view through a syringe of the first aspect of the first embodiment of the invention, FIG. 2 shows an enlarged sectional view (relative to FIG. 1) of the seal of the syringe shown in FIG. 1, FIG. 3 shows an enlarged side view (relative to FIG. 2) of an insert of the syringe shown in FIG. 1, FIG. 4 shows a top view of the insert of FIG. 3, FIGS. 5 to 8 inclusive show sectional views of part of a syringe in accordance with the second aspect of the first embodiment of the invention in different operational modes, FIGS. 9 to 11 inclusive show sectional views of part of a syringe in accordance with the third aspect of the first embodiment of the invention again in different operational modes, and FIGS. 12 to 14 inclusive show sectional views of part of a syringe in accordance with the second embodiment of the invention, again in different operational modes.

With reference to the drawings and to FIGS. 1 to 4 in particular, a syringe of the invention comprises a barrel 1 of circular cross-section and having a hollow needle 2 contained in an otherwise closed forward end thereof. A hollow cylindrical plunger 3 is contained within the barrel 1 and is slidably displaceable therein. At the forward, i.e. lower end as shown), of the plunger 3 is an extension portion 4.

Sealing means in the form of a circular rubber disc 5 (see FIG. 2 in particular) are connected to the barrel extension portion 4 by stretch fitting the former around the latter and ensuring retention by means of engagement between a lip 6 on the portion 4 and a lip 7 on the seal 5. These respective lips, however, allow for limited relative movement between the plunger 3 and the seal 5 along the axis of the barrel. The seal 5 has a cavity 8 in its lower surface and a circular aperture 9 linking the cavity with the upper surface of the seal. This aperture broadens out at the upper surface to form a well 10 which can accommodate a small lug 4A on the plunger extension portion 4.

Adapted for location in the cavity 8 of the seal 5 is an insert 11 (see FIGS. 3 and 4 in particular) but shown in a displaced position in FIG. 1. This insert comprises a main portion 12 whose size and shape corresponds to that of a cavity on the lower surface of the seal 5 and being disc-shaped overall with a central dimension 13 greater than that of either end face 14, 15. The insert therefore presents angled surfaces to a lip 16 of the cavity of the seal 5 during its introduction and displacement from the seal 5.

The insert 11 also has a supplementary portion 17 whose end 18 nearest the main portion 12 is cylindrical but whose end 19 remote from the main portion is cruciform in cross-section (see FIG. 4 in particular). The end 19 also has an enlarged flanged portion, again of cruciform cross-section. With the insert 11 in position in its cavity 8 in the seal 5, the main portion 12 and the end 18 are in sealing contact with the cavity 8 and the circular aperture 9 of the seal 5 respectively.

The sealing means as a whole, therefore, is in sealing engagement with the inside wall of the barrel 1 and defines a dispensing chamber 20.

Supplementary features of the syringe are an internal flange 21 of the barrel 1 as shown in the enlarged portion of FIG. 1 in particular and an external flange 22 on the lower end of the plunger 3 and, in addition, an external lug 23 on the plunger 3 and a complementary groove 24 at the top of the barrel 1. Engagement between this lug and this groove can be achieved by rotation of the plunger within the barrel. In addition the depression 25 at the base of the chamber 20 allows the plunger to be fully inserted into the chamber during the injection stage despite the displacement of the insert 11 from the cavity 8.

As supplied for use, the syringe will have the insert contained within the cavity 8 in the seal 5 with the insert portion 17 protruding upwards into the space formed beneath the plunger. In addition, the lug 23 will not be aligned with the groove 24 to prevent the plunger from being inserted completely into the barrel.

When ready for a first use, the lug 23 and the groove 24 are aligned and the needle 2 is inserted into a reservoir of fluid to be injected. Partial withdrawal of the plunger from the barrel therefore causes the fluid to be drawn into the dispensing chamber formed at the base as shown) of the barrel by the seal 5. By virtue of the shape of the insert and, in particular, the relative sizes of the areas of the insert a) exposed to atmospheric pressure on the side of the sealing means remote from the dispensing chamber and b) trapped in the cavity 8 in the seal 5 by the lip 15 in particular, the insert is not displaced. When sufficient fluid has been drawn into the dispensing chamber, all air is removed and the correct dose set by turning the syringe so that the needle is uppermost and effecting a slight forward displacement of the plunger. In general, during forward movement of the plunger, the force exerted on the top of the insert by the plunger and by the lug 4A on the plunger extension in particular is sufficient to displace the insert from its cavity in the seal. However, the end 19 of the insert is retained in the aperture 9 in the seal by means of the flanged end of the portion 19 contacting the base of the well 10.

The integrity of the seal during the plunger injection stage is achieved by interference between the projecting lug 4A on the end of the plunger extension 4 and the sides of the well 10 and also by contact between the lower end of the plunger and the surface of the seal surrounding the well.

However, once the plunger is withdrawn again, the contact between the lower end of the plunger and the seal is broken owing to the relative movement allowed between them and the insert cannot act to re-form the integrity of the seal by virtue of the cruciform nature of the insert end 19, thereby forming an air passageway (via the cruciform shape and air inlet ports 25 in the plunger communicating to atmosphere) and hence preventing refilling by the lack of formation of a vacuum in the dispensing chamber.

Any attempts to replace the insert into the seal by hand would be thwarted by the users' inability to withdraw fully the plunger from the barrel because of engagement between the respective lugs 21, 22.

Turning to FIGS. 5 to 8 inclusive, the syringe shown therein comprises a barrel 31 of circular cross-section and having a needle 32 contained in an otherwise closed end thereof. A cylindrical plunger 33 is contained within the barrel 31 and is slidably displaceable therein. At the forward, i.e. lower end (as shown), of the plunger 33 is a plunger extension portion 34 and further portions 35, 36. Of these, portion 36 is of circular cross-section whereas portions 34, 35 are of cruciform cross-section, i.e. of the type shown in FIG. 4.

Sealing means in the form of a cylindrical rubber seal 37 are mounted about the plunger extension portions. The outer surface of the seal 37 forms a seal with the inside surface of the barrel 31 (except for a central portion where there is a small air gap) and the internal surface of the seal 37 is loosely fitted about the cruciform shapes of plunger extension portions 34 and 35. The seal 37 is slidably displaceable within the barrel 31 and the plunger extension is slidably displaceable within the seal 37 within the limit defined by the abutment of a flange 38 with an upper (as shown) surface of the portion 35.

Mounted about the circular cross-section plunger portion 36 is a cylindrical rubber insert 39 of a size which causes its outer surface to fit closely, and form a seal with, the circular internal surface of seal 37. The insert 39 contains a circular slit 40 which causes an upper end (as shown) of the insert in an unconfined, i.e. free, state to splay—see FIG. 7—about the slit 40.

In use of the syringe, the mode shown in FIG. 5 is that in which the syringe is supplied and is a first withdrawal mode in which liquid can be drawn into a dispensing chamber 41 beneath the insert 39 from a reservoir and through the needle 32 by relative movement between the plunger 33 and the barrel 31 in the direction of the arrow. The integrity of the dispensing chamber 41 is maintained in this mode by the seals between the barrel 31 and the seal 37, the seal 37 and the insert 39 and between the insert 39 and the plunger portion 36.

In the first injection stage shown in FIG. 6 the plunger is moved downwards as shown by the arrow and this causes at the beginning of the movement the plunger to move relative to the seal 37 to the position shown in FIG. 6. The integrity of the dispensing chamber 41 is retained however because of the same seals as noted above. Injection of the liquid through the needle can therefore be effected.

However, in the second withdrawal mode shown in FIG. 7, an attempt to suck more fluid from the reservoir into the dispensing chamber is thwarted by the movement of the plunger in the direction shown by the arrow during which the insert 39 remains in position at the base (as shown) of the seal 37 and therefore is disengaged from the plunger portion 36. An air passageway therefore now exists between the dispensing chamber and the atmosphere via the interior of the unit 39, between the cruciform cross-section portions 34, 35 and the seal 37, between the lower surface (as shown) of the plunger and the upper surface (as shown) of the seal 37 (by virtue of grooves on the lower surface of the plunger) and between the plunger and the inside surface of the barrel.

Furthermore, at the start of a second injection mode as shown in FIG. 8, the splayed top of the insert 39 causes the lower end (as shown) of the plunger portion 36 to displace the insert 39 from the seal 37 completely, thus preventing injection by ensuring that fluid is preferentially displaced upwardly as shown in the drawings instead of via the needle.

Turning to FIGS. 9 to 11, a syringe of the invention comprises a barrel 51 having extension means 52 within which a hollow needle (not shown) of standard design may be mounted. A plunger 53 of hollow, cylindrical shape is slidable within the barrel and has a solid end portion 54 to which is secured a plunger extension 55.

This plunger extension 55 comprises a first portion 55A of circular cross-section, a second portion 55B of substantially oval cross-section and a third portion 55C which is frusto-conical in shape with its largest cross-section being adjacent the portion 55B.

Associated with the plunger is a sealing means in the form of a generally cylindrical elastomeric seal 56 having two main annular sealing surfaces 56A, 56B in sliding contact with the inside wall of the barrel 51.

The internal bore of the seal 56 comprises a first portion 56C of circular cross-section and of a size slightly larger than the major diameter of the oval cross-section plunger portion 55B but slightly smaller than the diameter of the circular cross-section plunger portion 55A, and a second portion 56D of generally frusto-conical shape and of a size corresponding at its larger cross-section end to that of the plunger portion 55C.

However, that part of the seal bore second portion 56D below the level of the plunger portion 55C as shown in FIG. 9 is castellated as shown in all the drawings.

In use, the syringe will generally be supplied in the form shown in FIG. 9. The plunger is in a first position relative to the seal 56 with the plunger portion 55C being in close contact with the non-castellated upper end (as shown) of seal portion 56D. The presence of this plunger portion in the cavity formed by the seal portion 56D thereby maintains the integrity of the seal as a whole.

Retraction of the plunger from the barrel therefore can allow injection fluid to be drawn in to a dispensing chamber 57 defined between the seal and the lower part (as shown) of the barrel. When the correct dosage of fluid has been drawn in and all air removed, etc., the injection stage can be commenced by moving the plunger forwardly within the barrel to cause it to adopt its second position relative to the seal 56, i.e. this forward movement of the plunger as a whole causes the plunger portion 55C to "pop out" of the cavity formed in the elastomeric seal 56 and adopt the position shown in FIG. 10.

However, during the remainder of the injection stage, fluid in the chamber 57 continues to be dispensed because of the interengagement of the base portion 54 and the seal 56 and, in particular, of the circular plunger portion 55A and the bore of the seal 56 as shown in FIG. 10.

Once the fluid has been dispensed in a first use of the syringe, any attempts to refill the syringe by creation of a vacuum in the chamber 57 in any subsequent use will be thwarted because the respective frusto-conical shapes of the seal bore and plunger portion 55C will not allow replacement of the portion 55C in the cavity of the bore and, moreover, the castellations in the lower end (as shown) of the bore allow air to be drawn into the chamber around the plunger end portion 54, around the oval cross-section plunger portion 55B and via the castellation as shown in FIG. 11.

Turning to FIGS. 12 to 14, this syringe of the invention comprises a barrel 61 having a cylindrical main portion of relatively large diameter and a reduced diameter forward end portion 62. This reduced diameter forward end portion 62 of the barrel is fitted with a needle 63 by appropriate means, for example including a seal as shown schematically at 64. A locking mechanism may be provided to secure the needle to the barrel.

Within the barrel 61 is positioned a plunger 65 which comprises a hollow cylindrical tube provided with one or more holes 66 through its wall. Encircling the forward end of the plunger 65 is a sealing ring 67 which is secured to the external surface of the plunger and which is slidable with the plunger within the barrel 61. Secured within the forward end of the plunger 65 is a plate 68 which is provided with a forwardly projecting stub 69 which carries a pin or blade 70. The tip of this pin or blade 70 is substantially in alignment with the forward end of the plunger 65. Fixed to the forward end of the plunger 65 is a diaphragm 71. This can be secured to the plunger 65 by any suitable means. For example, it may be glued into an annular recess in or around the front end of the plunger. The material of which the diaphragm 71 is made, and its dimensions, are such that the diaphragm is capable of changing its configuration as the plunger is moved in use. Although not shown in the drawing, the plate 68 is provided with an air passageway through its thickness so that the rearward side of the diaphragm 71 is in communication with the ambient atmosphere, via the holes 66.

In use, starting from the rest position as shown in FIG. 12, where the diaphragm 71 lies transversely to the axis of the plunger and clear of the pin 70, the initial movement is a retraction of the plunger to draw liquid into the syringe. This is shown in FIG. 13, where liquid is drawn up through the needle 63, into the dispensing chamber which is defined by the volume within the barrel forwardly of the plunger 65. Because of the fact that the needle 63 has a much smaller internal diameter than the internal diameter of the barrel 61, this retraction of the plunger causes the diaphragm 71 to move to a convex configuration relative to the plunger, as is shown clearly in FIG. 13. This ensures that the diaphragm is kept well away from the pin 70 during this movement. Subsequently, as shown in FIG. 14, when the plunger is depressed to expel liquid from the dispensing chamber, the relatively high pressure which is generated in the dispensing chamber in front of the diaphragm 71, because of the relative diameters of the needle and barrel, causes the diaphragm 71 to be pushed back into a generally V-shaped configuration, thus causing it to be punctured by the pin or cutter 70. It is important that the puncturing, or its equivalent, does not immediately destroy the seal, i.e. that the dispensing operation can be performed. It is only when the plunger is then retracted again that the disabling becomes effective. This physical damage to the diaphragm means that the integrity of the dispensing chamber is destroyed in terms of being able to maintain pressure within it, and the syringe is then no longer effective for a subsequent dispensing operation.

Various alternative features may be incorporated into the syringe of this embodiment. For example, instead of using a single pin or blade as the means to puncture the diaphragm 71, a plurality of needles, pins, blades, etc. could be used. Alternatively, chemical means could be employed to destroy the integrity of the diaphragm. A chemical product which would react with the material of the diaphragm could be positioned, for example on a flat plate behind the diaphragm, so that as the plunger is depressed the chemical is deposited on the diaphragm and will react with it to cause physical damage sufficient to destroy its sealing effect.

It is also not necessary that the diaphragm should be positioned on the forward end of the plunger. The diaphragm could be positioned anywhere along the length of the hollow plunger, or indeed within the barrel separate from the plunger.

It may also be desirable to provide a flow restrictor for the needle, in order to ensure that a sufficiently high pressure is generated in the dispensing chamber in front of the plunger to cause the diaphragm to be pushed back into the position in which it is punctured.

We claim:

1. A syringe comprising a barrel with means for positioning a needle at a forward end thereof, a plunger displaceable within the barrel, sealing means to maintain the integrity of a dispensing chamber forwardly of the barrel, and disabling means in the form of an insert which is adapted for displacement within the sealing means during a first use of the syringe and thereby subsequently render the sealing means inoperative in any attempted re-use of the syringe, the insert being substantially plate shaped and being manufactured from a more rigid material than that of the sealing means.

2. A syringe according to claim 1, in which the insert has an extension portion which, on displacement of the insert, is retained by the sealing means.

3. A syringe comprising a barrel with means for positioning a needle at a forward end thereof, a plunger displaceable within the barrel, sealing means to maintain the integrity of a dispensing chamber forwardly of the barrel and including a flexible diaphragm which defines part of the contour of the dispensing chamber and flexes rearwardly in response to increased pressure within the dispensing chamber as the plunger is depressed, and disabling means comprising puncturing means permanently and fixedly secured to the sealing means and arranged to puncture the diaphragm solely by rearward flexing of a portion of the diaphragm relative to the plunger when the plunger is depressed, thereby to destroy the sealing function of the sealing means.

4. A syringe according to claim 3, in which the puncturing means comprises at least one pin or blade positioned at the forward end of the plunger.

5. A syringe according to claim 3, in which the diaphragm is positioned across the forward end of the plunger and is capable of displacement from a convex configuration when the plunger is being withdrawn to a concave configuration when the plunger is depressed.

6. A syringe comprising a barrel with means for positioning a needle at a forward end thereof, a plunger axially displaceable within the barrel, sealing means which is carried by the forward end of the plunger so as to seal within the barrel and define a dispensing chamber forwardly thereof and which is free to make a limited axial movement relative to the plunger as the plunger is operated, and disabling means carried slidably within the sealing means and which initially seals between the plunger and the sealing means and which is operable by said relative movement between the plunger and sealing means to slide within and relative to the sealing means and which is operable upon reverse movement of the plunger to break the seal between the plunger and the disabling means so as to render the sealing means ineffective upon reverse movement of the plunger at any point along the path of the plunger.

7. A syringe comprising a barrel with means for positioning a needle at a forward end thereof; a plunger axially displaceable within the barrel; sealing means which is carried at the forward end of the plunger so as to seal within the barrel and define a dispensing chamber forwardly thereof and which is axially moveable relative to the plunger so as to make a limited movement in the opposite direction to the plunger as the plunger is first operated to dispense fluid from the dispensing chamber and the subsequently once movement of the plunger is reversed; and disabling means which cooperates with the plunger and sealing means so as to form a seal therebetween as the plunger is first operated to dispense fluid from the dispensing chamber, said disabling means being moved axially by the plunger to a disabling position relative to the sealing means as the sealing means makes said limited movement when the plunger is first operated to dispense fluid from the dispensing chamber, and said disabling means remaining in said disabling position once the plunger is reversed, thereby breaking said seal between the plunger and the sealing means, whereby said disabling means is effective at any point along the path of the plunger.

8. A syringe as claimed in claim 7, in which the sealing means comprises a hollow seal element mounted about the forward end of the plunger, and the disabling means comprises an insert that is received as an interference fit within the hollow seal element and is held in the disabling position by virtue of said interference fit.

9. A syringe as claimed in claim 8, in which the insert has an annular shape and fits over an axial projection from the forward end of the plunger to form said seal between the plunger and the sealing means.

10. A syringe as claimed in claim 9, in which a circular slit is formed in the rearwardly directed face of the annular insert so as to from a lip about the central aperture that splays inwards when said axial projection of the plunger is removed from said aperture, thereby preventing re-engagement of said axial projection of the plunger in said aperture.

* * * * *